United States Patent [19]

Stahly

[11] Patent Number: 4,798,900

[45] Date of Patent: Jan. 17, 1989

[54] PRODUCING BIS(ALICYCLIC) THIOETHERS

[75] Inventor: G. Patrick Stahly, Baton Rouge, La.

[73] Assignee: Ethyl Corporation, Richmond, Va.

[21] Appl. No.: 917,773

[22] Filed: Oct. 10, 1986

[51] Int. Cl.$^4$ .................. C07D 209/48; C07D 307/89; C07C 51/36

[52] U.S. Cl. .................................. 548/461; 549/241; 560/118; 562/500

[58] Field of Search .................. 548/461; 549/241; 560/118; 562/500

[56] References Cited

U.S. PATENT DOCUMENTS 3,989,712 11/1976 Williams .............................. 548/461

OTHER PUBLICATIONS

Derwent Abstract of Japanese Patent J5 5069-572 published May 26, 1960.
Fieser and Fieser, *Reagents for Organic Synthesis*, Wiley Inter-Science Pub., N.Y., 1969, 2, 389–90.
Charlton et al, *Can. J. Chem.*, 1973, 51, 1852–6.
Williams, et al, *J. Org. Chem.* 1977, 42, 3414–9.
Evans et al., *Polymer Preprints (American Chemical Society, Div. Polymer Chem.)* 1984, 25, 268–9.
Tsuji et al., *Bull. Chem. Soc. Jpn.*, 1985, 58, 1603∝4.
Chou et al., *J. Chem. Soc. Chem. Commun.*, 1985, 236–7.
Chemical Abstracts, 1986, 104, p. 11, Abstract No. 104:130428x Abstract of General Electric Company, Jpn. Kokai Tokkyo Koho JP 60,188,368.
Cava et al., *J. Am. Chem. Soc.*, 1959, 81, 4266–8.
Cope et al., *J. Am. Chem. Soc.*, 1961, 83, 3859–61.
Gundermann et al., *Angew. Chem. Internat. Ed.*, 1966, 5, 668.

*Primary Examiner*—Mary E. Ceperley
*Attorney, Agent, or Firm*—John F. Sieberth

[57] ABSTRACT

3,3'-Thiobis(2,5-dihydrothiophene-1,1-dioxides) on heating with a reactive Diels-Alder dienophile undergo a reaction producing thioethers having two six-membered alicyclic rings in the molecule, such as 4,4'-thiobis(3,6-dihydrophthalic acids) or the esters, anhydrides or imides thereof, and 4,4'-thiobis(1,2,3,6-tetrahydrophthalic acids) or the esters, anhydrides or imides thereof. Both rings of the dihydrothiophene dioxides participate in the reaction, apparently by forming a tetraene structure which co-reacts with two equivalents of the dienophile to form an adduct in which each six-membered ring has one or two olefinic double bonds. During the course of the reaction, the thioether bridge remains intact. Some of the bis(alicyclic) thioethers are readily converted to the corresponding bis(aromatic)-thioethers by use of known aromatization methods and systems. Various utilities for the products of the foregoing reactions are described.

12 Claims, No Drawings

PRODUCING BIS(ALICYCLIC) THIOETHERS

BACKGROUND

The only published route to 4,4'-thiobis(phthalic acid) derivatives involves treatment of 4-substituted N-alkylphthalimides with sodium sulfide followed by hydrolysis and dehydration. See Evans et al, *Polymer Preprints (American Chemical Society, Div. Polymer Chem.)* 1984, 25, 268. Preparation of the starting materials for this route most readily requires electrophilic substitution reactions of phthalic anhydride followed by separation of 3- and 4-substituted isomers and imide formation. See Williams et al, *J. Org. Chem.* 1977, 42, 3414.

THE INVENTION

This invention involves the discovery, inter alia, that 3,3'-thiobis(2,5-dihydrothiophene-1,1-dioxides) on heating with a reactive Diels-Alder dienophile undergo a reaction producing thioethers having two six-membered alicyclic rings in the molecule, such as 4,4'-thiobis(3,6-dihydrophthalic acids) or the esters, anhydrides or imides thereof, and 4,4'-thiobis(1,2,3,6-tetrahydrophthalic acids) or the esters, anhydrides or imides thereof. Both rings of the dihydrothiophene dioxides participate in the reaction, apparently by forming a tetraene structure which co-reacts with two equivalents of the dienophile to form an adduct in which each six-membered ring has one or two olefinic double bonds. During the course of the reaction, the thioether bridge remains intact.

The utility of similar 2,5-dihydrothiophene-1,1-dioxides—which of course do not contain a thioether bridge—as masked dienes in Diels-Alder reactions is well established. See Tsuji et al., *Bull. Chem. Jpn.*, 1985, 58, 1603;
Chou et al, *J. Chem. Soc., Chem. Comm.*, 1985, 236;
Charlton et al, *Can. J. Chem.*, 1973, 51, 1852;
Fieser and Fieser, *Reagents for Organic Synthesis*, Wiley Interscience Pub., N.Y., 1969, 2, 668;
Gundermann et al, *Angew. Chem. Internat. Ed.*, 1966, 5, 668;
Cope et al., *J. Am. Chem. Soc.*, 1961, 83, 3859; and
Cava et al., *J. Am. Chem. Soc.*, 1959, 81, 4266.

The bis(alicyclic) thioethers produced by the above process can be used for a number of applications. For example, they can be used as pesticides, herbicides and plant growth regulants. In addition they may be employed as extreme pressure additives and corrosion inhibitors in lubricating oils, especially when used in the form of imides or esters. Some of the bis(alicyclic) thioethers are readily converted to the corresponding bis(aromatic)thioethers by use of known aromatization methods and systems such as are described or referred to in March, Advanced Organic Chemistry, John Wiley & Sons, New York, 1985, pages 1052–1054 (and references cited therein), and Fatma, et al., *J. Chem. Res.* (M), 1984, 2658. (It will be understood of course that the presence of the divalent sulfur in the thioethers precludes use of precious metal catalysts for effecting aromatization.) Thiobis(phthalimides) and thiobis(phthalic anhydrides), which can be formed in this manner, have been reported to be useful as antioxidants in rubber, hydrocarbon oils, polypropylene, etc., as curing agents for epoxy resins, as intermediates for polyester resins or polythioetherimides, as plasticizers, and as fire retardants—see U.S. Pat. No. 3,989,712; Japan Kokai Tokkyo Koho No. 60,188,368 (25 Sep 1985) [*Chemical Abstracts* 104:130428x]; and Evans et al, *Polymer Preprints (American Chemical Society,* Div. Polymer Chem.), 1984, 25(1) 268–269. In some instances use of conventional aromatization techniques results not in aromatization of the six-membered rings, but in formation of six-membered diene ring systems. These products may be used as antioxidants, as corrosion inhibitors and as pesticides, herbicides and plant growth regulants. And the bis(alicyclic) thioethers formed by the process of this invention can readily be converted to the corresponding sulfones, which may be used as rust inhibitors, pesticides, herbicides, and plant growth regulants.

The specific type of product formed in the above process is dependent upon the type of dienophile used in the reaction. For example, maleic anhydride and its hydrocarbon-substituted congeners (citraconic anhydride, dimethylmaleic anhydride, phenylmaleic anhydride, etc.) give rise to the formation of 4,4'-thiobis(1,2,3,6-tetrahydrophthalic anhydrides). Maleic acid and its hydrocarbon-substituted congeners (citraconic acid, etc.) form 4,4'-thiobis(1,2,3,6-tetrahydrophthalic acids), whereas the esters of maleic acid and its hydrocarbon-substituted congeners produce 4,4'-thiobis(1,2,3,6-tetrahydrophthalic acid esters).

When the dienophile is maleimide, a hydrocarbon substituted congener thereof (e.g., 2-methylmaleimide, 2,3-dimethylmaleimide, etc.) or an N-substituted maleimide in which the substituent is a carbon-bonded organo group (e.g., N-methylmaleimide, N-phenylmaleimide, N-p-tolylmaleimide, N-cyclohexylmaleimide, N-ethyl-2-methylmaleimide, etc.), the product of the reaction is a 4,4'-thiobis(1,2,3,6-tetrahydrophthalimide) in which each nitrogen atom is substituted by a hydrogen atom or by the N-organo substituent of the N-substituted maleimide.

Use of acetylene dicarboxylic acid or its esters as the dienophile results in the production of 4,4'-thiobis(3,6-dihydrophthalic acid) or its esters.

If the dienophile is bromomaleic acid or bromomaleic anhydride or an ester of bromomaleic acid, the product of the reaction is 4,4'-thiobis(3,6-dihydrophthalic acid) or 4,4'-thiobis(3,6-dihydrophthalic anhydride) or an ester of 4,4'-thiobis(3,6-dihydrophthalic acid).

Any unsaturated compounds may be used that participate in Diels-Alder reactions, such as those containing the C=CX group, where X=CHO, COR, COOH, COOR, COCl, COAr, CN, $NO_2$, Ar, $CH_2Cl$, $CH_2NH_2$, $CH_2CN$, $CH_2COOH$, halogen, and the like as referred to in Holmes, *Org. React.*, 4, 60–173 (1948), the disclosure of which is incorporated herein by reference.

The 3,3'-thiobis(2,5-dihydrothiophene-1,1-dioxides) used in the process may be represented by the general formula

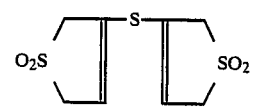

wherein the rings may be substituted by inert substituents such as alkyl, cycloalkyl, aryl, aralkyl, cycloalkylalkyl, and the like. The substituents should of course be positioned and sized so that they do not prevent the desired cyclization reaction by virtue of steric hindrance. Methods suitable for the synthesis of such compounds are reported in the literature, e.g., Lewis and Emmons, *J. Org. Chem.* 1966, 31, 3572, all disclosure of which is incorrated herein by reference. Use of 3,3'-thiobis(2,5-dihydrothiophene-1,1-dioxide itself is preferred because of the ready availability and low cost of butadiene sulfone (3-sulfolene), the raw material from which 3,3'-thiobis(2,5-dihydrothiophene-1,1-dioxide is produced.

When heating 3,3'-thiobis(2,5'-dihydrothiophene-1,1-dioxide to temperatures within the range of 100° to 200° C. a thiotetraene, viz., 2,2'-thiobis(1,3-butadiene), is produced. The formation of this thiotetraene was observed by GC/MS analysis. Attempts to isolate the thiotetraene resulted in polymerization even in the presence of a polymerization inhibitor.

To conduct the reaction between the 3,3'-thiobis(2,5-dihydrothiophene-1,1-dioxide and the dienophile, one should heat the system to a temperature sufficient to cause cyclization to occur. By analogy with the thiotetraene formation, the temperature is preferably maintained between about 100° and about 200° C. whereby presumably the thiotetraene is formed as a transitory intermediate which undergoes cyclization with the dienophile whereby two six-membered rings are formed with the thiotetraene molecule. Most preferably temperatures of at least about 140° C. and no higher than about 200° C. are used, as this provides a suitably rapid rate of reaction.

It is convenient to conduct the reaction in an indifferent (innocuous; inert) liquid solvent such as a paraffinic, cycloparaffinic or aromatic hydrocarbon, dimethylsulfoxide, dimethylformamide, dimethylacetamide, tetrahydrofuran, diglyme, dibutyl ether, a chlorinated hydrocarbon, acetonitrile, an organic alcohol, ethyl acetate, and the like.

The following examples are illustrative of the practice of various embodiments of this invention. In the Examples: Melting points were determined with a Fisher-Johns hot stage or a Mel-Temp melting point apparatus and are uncorrected. NMR spectra were recorded on a Varian EM-390 or a GE/NIC NT-360 spectrometer. Chemical shifts are reported in parts per million relative to tetramethylsilane. Infrared spectra were recorded on a Perkin Elmer 983 spectrophotometer. Mass spectra were obtained on a Finnigan 4023 gas chromatograph/mass spectrometer equipped with a 50-m SE-52 fused silica capillary column. Elemental analyses were performed by Galbraith Laboratories, Knoxville, TN.

Examples 1 through 10 illustrate methods for the synthesis of thioether bridged di- and tetrahydrophthalic acid derivatives, such as the esters, anhydrides, and imides thereof.

EXAMPLE 1

4,4'-Thiobis(1,2,3,6-Tetrahydrophthalic Anhydride)

A mixture of 10.0 g (37.5 mmol) of 3,3'-thiobis(2,5-dihydrothiophene-1,1-dioxide) (DTS) and 7.35 g (75.0 mmol) of maleic anhydride in 25 mL of mixed xylenes (bp 139°–142° C.) was heated at reflux for 2 hours and allowed to cool to room temperature. After decantation of the xylenes the lower, oily layer was dissolved in 25 mL of hot dichloromethane. The resulting brown solution was filtered through glass fiber paper, reduced in volume to 20 mL by distillation, and cooled to yield 4.06 g (32% yield) of a higher-melting isomer of 4,4,-thiobis(1,2,3,6-tetrahydrophthalic anhydride): mp 180°–182° C.; $^1$H NMR (CDCl$_3$) 2.40–2.74 (m, 8H), 3.47–3.64 (m, 4H), 5.95–6.01 (m, 2H); $^{13}$C NMR (DMSO-d$_6$) 24.9(t), 28.8(t), 39.1(d), 40.3(d), 128.5(d), 130.9(s), 174.5(s), 175.0(s); IR (KBr) 3433 (H$_2$O), 2960, 1841, 1773, 1714, 1331, 1311, 1234, 1193, 1100, 1086, 1009, 967, 938, 925 cm$^{-1}$. Anal. Calcd. for C$_{16}$H$_{14}$O$_6$S: C, 57.48; H, 4.22. Found C, 57.29; H, 4.17.

Addition of diethyl ether to the mother liquor and cooling afforded 2.16 g (17%) of a lower-melting isomer of 4,4'-thiobis(1,2,3,6-tetrahydrophthalic anhydride): mp 166°–169° C.; $^1$H NMR (CDCl$_3$) 2.40–2.73 (m, 8H), 3.45–3.65 (m, 4H), 6.05–6.15 (m, 2H); $^{13}$C NMR (DMSO-d$_6$) 25.0(t), 28.6(t), 40.0(d), 40.2(d), 129.2(d), 130.7(s), 174.6(s), 175.0(s); IR (KBr) 3425 (H$_2$O), 2942, 1845, 1774, 1716, 1242, 1225, 1199, 1102, 1091, 1035, 1009, 966, 941, 925, cm$^{-1}$ Anal Calcd. for C$_{16}$H$_{14}$O$_6$S.1/2H$_2$O: C, 55.97; H, 4.40. Found: C, 56.11; H, 4.42.

Concentration of the mother liquor gave 4.73 g of brown glass.

EXAMPLE 2

4,4'-Thiobis(1,2,3,6-Tetrahydrophthalimide)

A mixture of 1.0 g (3.8 mmol) of DTS and 0.73 g (7.5 mmol) of maleimide in 3 mL of mixed xylenes (bp 139°–142° C.) was heated at reflux for 1 hour and allowed to cool to room temperature. After decantation of the xylenes the remaining off-white solid was triturated with 15 mL of boiling dichloromethane and filtered to give 1.2 g of white solid. Crystallization from methanol afforded 0.80 g (64% yield) of 4,4'-thiobis(1,2,3,6-tetrahydrophthalimide): mp 204°–208° C.; $^1$H NMR (CDCl$_3$/DMSO-d$_6$) 2.20–2.55 (m, 8H), 3.05–3.20 (m, 4H), 5.80–5.87 (m, 1H, isomer a), 5.95–6.00 (m, 1H, isomer b); $^{13}$C NMR (Me$_2$SO-d$_6$), paired signals due to isomer mixture, 24.7 and 24.9 (t), 28.7 and 28.9 (t), 39.4 and 39.5 (d), 40.5 and 40.6 (d), 128.2 and 129.1 (d), 130.9 and 131.0 (s), 180.5 and 180.6 (s), 181.1 and 181.2 (s); IR (KBr) 3431, 3207, 2927, 1781, 1703, 1359, 1336, 1314, 1176, 787, 577 cm$^{-1}$. Anal. Calcd. for C$_{16}$H$_{16}$N$_2$O$_4$S.1/2H$_2$O: C, 56.29; H, 5.02, N, 8.21. Found: C, 56.68; H, 5.18, N, 8.16.

EXAMPLE 3

4,4'-Thiobis(N-Phenyl-1,2,3,6-Tetrahydrophthalimide)

A mixture of 5.0 g (19 mmol) of 3,3'-thiobis(2,5-dihydrothiophene-1,1-dioxide) and 6.5 g (38 mmol) of N-phenylmaleimide in 20 mL of mixed xylenes (bp 139°–142° C.) was heated at reflux for 1 hour and allowed to cool to room temperature to give a gel. This was warmed with stirring until a slurry resulted. Filtration afforded a solid which was dissolved in 100 mL of hot dichloromethane and filtered through a glass fiber paper. The filtrate was reduced in volume to 50 mL by distillation, treated with diethyl ether, and cooled to give 3.0 g (33% yield) of 4,4'-thiobis(N-phenyl-1,2,3,6-tetrahydrophthalimide): mp 212°–217° C.; $^1$H NMR (CDCl$_3$) 2.42–2.80 (m, 8H), 3.19–3.32 (m, 2H), 5.95–6.02 and 6.10–6.19 (m, 2H, 2 isomers), 7.20–7.50 (m, 10H); $^{13}$C NMR (CDCl$_3$), paired signals due to isomer mixture, some aromatic signals overlap, 25.3 and 25.6 (t), 29.1 and 29.7 (t), 38.6 and 38.8 (d), 39.6 and 39.8 (d), 126.2 (d), 126.3 (d), 128.6 (d), 128.8 (s), 129.1 (d), 129.5 (s); IR (KBr) 3453 (H$_2$O), 2918, 1709, 1597, 1494, 1381, 1199, 1180, 769, 694, 586 cm$^{-1}$. Anal. Calcd. for C$_{28}$H$_{24}$N$_2$O$_4$S.1/2H$_2$O: C, 6813; H, 5.11; N, 5.68. Found: C, 68.24; H, 5.22; N, 5.69.

The mother liquor was stripped of solvent in vacuo to give 2.5 g of brown solid. NMR analysis indicated this contained mostly 4,4'-thiobis(N-phenyl-1,2,3,6-tetrahydrophthalimide).

EXAMPLE 4

44'-Thiobis(3,6-Dihydrophthalic Anhydride)

A mixture of 1.0 g (3.8 mmol) of DTS, 1.7 g (7.5 mmol) of bromomaleic anhydride, and 6 mL of mixed xylenes (bp 139°–142° C.) was heated to reflux for 1 hour. Vigorous foaming occurred and acidic fumes (presumably HBr) were given off. The mixture was allowed to cool to room temperature, filtered to remove a little brown powder, and the filtrate was concentrated in vacuo to give an orange semisolid. Trituration of this residue with 10 mL of boiling dichloromethane followed by filtration afforded 0.67 g (52% yield) of yellow, solid 4,4'-thiobis(3,6-dihydrophthalic anhydride): mp 227°–230° C. (with gas evolution); IR (KBr) 3436, 2923, 1842, 1787, 1691, 1415, 1263, 1061, 900, 714 cm$^{-1}$.

EXAMPLE 5

4,4'-Thiobis(3,6-Dihydrophthalic Anhydride)

A mixture of 1.0 g (3.8 mmol) of DTS, 1.7 g (7.5 mmol) of bromomaleic anhydride, 1.6 g (15 mmol) of sodium carbonate, and 6 mL of mixed xylenes (bp 139°–142° C.) was heated to reflux for 1 hour. Vigorous foaming occurred. The mixture was filtered hot and the solids were washed with 10 mL of toluene. The combined filtrates were concentrated in vacuo to give an orange solid. Trituration of this residue with 10 mL of boiling dichloromethane followed by filtration afforded 0.82 g (65% yield) of 4,4'-thiobis(3,6-dihydrophthalic anhydride).

EXAMPLE 6

4,4'-Thiobis(3,6-Dihydrophthalic Anhydride)

A solution of 0.50 g (1.9 mmol) of DTS and 0.85 g (3.8 mmol) of bromomaleic anhydride in 3 mL of dimethyl sulfoxide was heated at 130°–150° C. for 1 hour and allowed to cool to room temperature. Concentration in a stream of dry nitrogen afforded a residue which, by NMR analysis, contained 4,4'(thiobis(3,6-dihydrophthalic anhydride).

EXAMPLE 7

4,4'-Thiobis(Dimethyl 3,6-Dihydrophthalate)

Nitrogen was bubbled through a mixture of 5.09 g (19 mmol) of DTS and 5.4 g (38 mmol) of dimethyl acetylene dicarboxylate in 15 mL of mixed xylenes (bp 139°–142° C.) while it was heated to reflux by means of a hot oil bath for 1 hour. The mixture was cooled to room temperature and the xylenes were removed by distillation at 25 torr. The resulting viscous orange oil was purified by flash chromatography on 150 g of silica gel eluted with 0–1% methanol in dichloromethane to give 4.6 g (58% yield) of pale yellow, waxy 4,4'-thiobis(dimethyl 3,6-dihydrophthalate). An analytical sample was obtained by crystallization from toluene: mp 101-103 C; $^1$H NMR (CDCl$_3$); 3.04–3.20 (m, 8H), 3.81 (s, 12H); 5.95–6.08 (m, 2H); $^{13}$C NMR (CDCl$_3$) 29.5 (t), 31.5 (t), 52.1 (q. 2 carbons), 125.8 (s), 126.3 (d), 131.4 (s), 131.8 (s), 167.2 (s), 267.8 (s); IR (KBr) 3426 (H$_2$O), 2955, 1715, 1668, 1440, 1413, 1272, 1255, 1140, 1064, 952, 748 cm$^{-1}$. Anal. Calcd. for C$_{20}$H$_{22}$O$_8$S: C, 56.86; H, 5.25. Found: C, 56.76; H, 5.27.

EXAMPLE 8

4,4'-Thiobis(1,2,3,6-Tetrahydrophthalic Anhydride)

A mixture of 1.0 g (3.8 mmol) of DTS and 0.74 g (7.5 mmol) of maleic anhydride in 5 mL of toluene was heated at reflux for 2 hours and allowed to cool to room temperature. After decantation of the toluene the lower, oily layer was dissolved in 10 mL of dichloromethane. The resulting brown solution was filtered, reduced in volume to 4 mL by distillation, and cooled to yield 0.65 g (53% yield) of 4,4'-thiobis(1,2,3,6-tetrahydrophthalic anhydride).

EXAMPLE 9

4,4-Thiobis-(1,2,3,6-tetrahydrophthalimide)

A mixture of 25.0 g (93.9 mmol) of DTS, 18.2 g (188 mmol) of maleimide, and 75 mL of mixed xylenes (bp 139°–142° C.) was stirred vigorously and heated to reflux for 30 min. Decantation of the xylenes followed by trituration of the solid residue with 50 mL of dichloromethane afforded a white solid which was recrystallized from tetrahydrofuran-methanol to give 24.6 g (79% yield) of 4,4'-thiobis-(1,2,3,6-tetrahydrophthalimide) as a 1:1 mixture of isomers.

EXAMPLE 10

4,4'-Thiobis-(N-phenyl-1,2,3,6-tetrahydrophthalimide)

A mixture of 1.0 g (3.8 mmol) of DTS, 1.3 g (7.5 mmol) of N-phenylmaleimide, and 4 mL of mixed xylenes (bp 139°–142° C.) was heated at reflux for 1 h and allowed to cool to room temperature. After decantation of the xylenes the lower, oily layer was subjected to flash chromatography on 100 g of silica gel (eluted with 1% methanol in dichloromethane) to give 1.4 g (75% yield) of 4,4'-thiobis-(N-phenyl-1,2,3,6-tetrahydrophthalimide) as a 1:1 mixture of isomers.

Example 11 illustrates the use of the thioether bridged di- and tetrahydrophthalic acid derivatives, such as the esters, anhydrides, and imides thereof as intermediates in the synthesis of the corresponding sulfones.

EXAMPLE 11

4,4'-Bis(N-Phenyl-1,2,3,6-Tetrahydrophthalimide) Sulfone

A slurry of 1.0 g (2.1 mmole) of 4,4'-thiobis(N-phenyl-1,2,3,6-tetrahydrophthalimide) in 25 mL of glacial acetic acid and 5 mL of 30% hydrogen peroxide was heated at reflux for 30 minutes. During this time the mixture became homogeneous, then heterogeneous as a crystalline solid separated. The solid was removed by filtration, washed with 10 mL of water, 10 mL of 10% sodium carbonate, 20 mL of water, and 20 mL of absolute ethanol, and dried in vacuo to give 0.70 g (65% yield) of 4,4'-bis(N-phenyl(1,2,3,6-tetrahydrophthalimide) sulfone: mp 298°–299° C.; decomposition point (gas evolution) 330° C.; IR (KBr) 3451, 3080, 2960, 1703, 1493, 1385, 1305, (SO$_2$), 1195 (SO$_2$) cm$^{-1}$. Anal. Calcd. for C$_{28}$H$_{24}$N$_2$O$_6$S: C, 65.10; H, 4.68; N, 5.42. Found: C, 64.93; H, 4.80; N, 5.45.

Examples 12 through 16 illustrate the production of 4,4'-thiobis(phthalic acid) derivatives by aromatization of the thioether bridged di- and tetrahydrophthalic acid derivatives, and demonstrate the ease with which such aromatization can be effected using a 4,4'-thiobis(tetrahydrophthalimide having an organo substituent on each nitrogen atom or an ester of 4,4′-thiobis(3,6-dihydrophthalic acid).

EXAMPLE 12

4,4′-Thiobis(N-Phenylohthalimide)

A mixture of 200 mg (0.41 mmol) of 4,4′-thiobis(N-phenyl-1,2,3,6-tetrahydrophthalimide) and 53 mg (1.7 mmol) of elemental sulfur was heated to 240°–260° C. (sand bath) for 20 minutes and cooled to room temperature. The resulting brown residue was purified by preparative TLC on silica gel (eluent: 1% methanol in dichloromethane) to give 61 mg (31% yield) of 4,4′-thiobis(N-phenylphthalimide) as a yellow solid. Trituration with dichloromethane afforded a white solid: mp 275°–280° C.; (lit 293°–295° C.—see U.S. Pat. No. 3,989,712); IR (KBr) 3065, 1710,1375 cm$^{-1}$; $^1$H NMR (slurry in DMSO-d$_6$) 7.52 (m,5H), 7.97 (m, 3H).

EXAMPLE 13

4,4′-Thiobis(Dimethyl Phthalate)

A mixture of 200 mg (0.47 mmol) of 4,4′-thiobis(dimethyl 3,6-tetrahydrophthalate) and 213 mg (0.94 mmol) of 2,3-dichloro-5,6-dicyano-1,4-benzoquinone (0.94 mmol) in 2 mL of toluene was heated to reflux for 1 hour, allowed to cool to room temperature, and filtered to remove precipitated brown solids. The solids were washed with 1 mL of toluene and the combined filtrates were concentrated in vacuo. The residue was dissolved in 1 mL of dichloromethane and passed through a column of 1.0 g of neutral alumina (act. grade I). The column was washed with an additional 10 mL of dichloromethane. Combination and concentration of the eluents afforded 208 mg of 4,4′-thiobis(dimethyl phthalate) as a yellow oil (containing some toluene and dichloromethane by NMR analysis, theoretical yield is 198 mg): $^1$H NMR (CDCL$_3$) 3.92 (s, 6H), 7.47 (dd, 1H, J =8, 2Hz), 7.66 (d, 1H, J=2Hz), 7.74 (d, 1H, J=8Hz); $^{13}$C NMR (CDCl$_3$) 52.5 (q), 52.6 (q), 129.9 (d), 130.3 (s), 130.4 (d), 132.7 (d), 133.4 (s), 138.6 (s), 166.7 (s), 167.0 (s); IR (KBr) 3000, 2951, 1724, 1586, 1556, 1433, 1292, 1192, 1129, 1101, 1068, 969, 772 cm$^{-1}$. Anal. Calcd. for C$_{20}$H$_{18}$O$_8$S: C, 57.41: H, 4.34. Found: C, 57.09; H, 4.56.

EXAMPLE 14

4,4′-Thiobis(Dimethyl Phthalate)

A mixture of 200 mg (0.47 mmol) of 4,4′-thiobis(dimethyl 3,6-tetrahydrophthalate) and 31 mg (0.97 mmol) of elemental sulfur was heated to 215°–225° C. (sand bath) for 10 minutes and allowed to cool to room temperature. The resulting black oil was purified by preparative TLC on silica gel (eluent: 1% methanol in dichloromethane) to give 173 mg (87% yield) of 4,4′-thiobis(dimethylphthalate) as an orange oil.

EXAMPLE 15

4,4-Thiobis(N-phenylphthalimide)

A mixture of 100 mg (0.21 mmol) of 4,4′thiobis(N-phenyl- 1,2,3,6-tetrahydrophthalimide), 3 mg (0.03 mmol) of I$_2$, 1.6 mL(0.03 mmol) of 96% H$_2$SO$_4$, and 1 mL of dimethylsulfoxide was heated to 100° C. for 18 hours, allowd to cool to room temperature, and poured into 10 mL of water. The resulting precipitate was removed by filtration and washed with water and absolute ethanol. A TLC analysis of this material indicated the presence of 1,4′-thiobis(N-phenylphthalimide).

EXAMPLE 16

4,4′-Thiobis(Phthalic Anhydride)

A mixture of 100 mg (0.30 mmol) 4,4′-thiobis(3,6-dihydrophthalic anhydride), 3 mg (0.03 mmol) I$_2$, 1.6 mL (0.03 mmol) of 96% H$_2$SO$_4$, and 1 mL of dimethylsulfoxide was heated to 90°–100° C. for 2 hours and allowed to cool to room temperature to give a black solution. This was concentrated in a stream of dry nitrogen. An NMR spectrum of the residue indicated the presence of 4,4′-thiobis(phthalic anhydride).

Example 17 illustrates that use of ordinary aromatization procedures with some bis(alicyclic) thioethers such as 4,4′-thiobis(1,2,3,6-tetrahydrophthalic anhydride) tends to result in the formation of thioethers with diene ring systems.

EXAMPLE 17

4,4′-Thiobis(1,2-Dihydrophthalic Anhydride)

Warming of a slurry of 50 mg (0.15 mmol) of 4,4′-thiobis(1,2,3,6-tetrahydrophthalic anhydride) and 1 mL of tetrahydrofuran produced a nearly homogeneous solution that was allowed to cool to room temperature. This was treated with 41 mg (0.30 mmol) of N-bromoacetamide, stirred for 15 minutes, and treated dropwise with 42 mL (0.30 mmol) of triethylamine. The resulting heterogeneous mixture was stirred for a couple of minutes and diluted with 8 mL of water. Removal of the precipitated solid by filtration followed by drying in vacuo over phosphorus pentoxide afforded 19 mg (38% yield) of a solid: mp 218°–223° C.; IR (KBr) 3431, 2923, 1842, 1791, 1691, 414, 1262, 1061, 905, 713 cm$^{-1}$. The product was deemed to comprise 4,4′-thiobis(1,2-dihydrophthalic anhydride).

As indicated above, it is presumed that a tetraene is formed as an intermediate when the dihydrothiophene dioxides are heated in the presence of a suitable Diels-Alder dienophile. However attempts to isolate 2,2′-thiobisbutadiene (the intermediate from 3,3′-thiobis(2,5-dihydrothiophene-1,1-dioxide) were unsuccessful. Its probable existance in solution was indicated by GC/MS (note Example 18 below) but removal of the solvent by distillation resulted in deposition of a rubbery solid, even in the presence of a radical inhibitor.

Example 18 shows that DTS may be converted to 2,2′-thiobisbutadiene at relatively mild temperatures.

EXAMPLE 18

2,2′-Thiobisbutadiene

A mixture of 0.5 g of DTS and 2 mL of toluene was heated at reflux for 2 h. Examination of the solution by GC/MS revealed the presence of a single peak identified 2,2′-thiobisbutadiene: mass spectrum (70 eV), m/e (relative intensity) 138 (M+, 61), 137 (23), 123 (39), 105 (25), 97 (33), 85 (22), 79 (23), 71 (80), 59 (29), 58 (30), 53 (100), 51 (41), 50 (23), 45 (78), 39 (32).

This invention is susceptible to considerable variation in its practice, the descriptions and exemplifications given above being merely illustrative thereof. Accordingly, it is not intended that this invention be unduly limited by the foregoing disclosure. Rather, what is intended to be covered is within the spirit and scope of the ensuing claims.

What is claimed is:

1. A process of producing thioethers having two six-membered alicyclic rings in the molecule which comprises heating at a temperature in the range of 100° to 200° C. a reaction system composed of a 3,3'-thiobis(2,5-dihydrothiophene-1, 1-dioxide) and a reactive Diels-Alder dienophile so that cyclization occurs.

2. A process of claim 1 wherein the 3,3'-thiobis(2,5-dihydrothiophene-1,1-dioxide) is 3,3'-thiobis(2,5-dihydrothiophene-1,1-dioxide).

3. A process of claim 2 wherein the dienophile is maleic anhydride so that 4,4'-thiobis(1,2,3,6-tetrahydro phthalic anhydride) is produced.

4. A process of claim 2 wherein the dienophile is maleimide so that 4,4'-thiobis(1,2,3,6-tetrahydrophthalimide) is produced.

5. A process of claim 2 wherein the dienophile is an N-organo substituted maleimide so that a 4,4'-thiobis(1,2,3,6-tetrahydrophthalimide) having an organo substituent on each nitrogen atom is produced.

6. A process of claim 2 wherein the dienophile is an N-phenyl maleimide so that a 4,4'-thiobis(N-phenyl-1,2,3,6tetrahydrophthalimide) is produced.

7. A process of claim 2 wherein the dienophile is N-phenyl maleimide so that 4,4'-thiobis(N-phenyl-1,2,3,6-(tetrahydrophthalimide) is produced.

8. A process of claim 2 wherein the dienophile is acetylene dicarboxylic acid so that 4,4'-thiobis(3,6-dihydrophthalic acid) is produced.

9. A process of claim 2 wherein the dienophile is an ester of acetylene dicarboxylic acid so that an ester of 4,4'-thiobis(3,6-dihydrophthalic acid) is produced.

10. A process of claim 2 wherein the dienophile is a dialkyl ester of acetylene dicarboxylic acid so that a dialkyl ester of 4,4'-thiobis(3,6-dihydrophthalic acid) is produced.

11. A process of claim 2 wherein the dienophile is dimethyl acetylene dicarboxylate so that 4,4,-thiobis(dimethyl 3,6-dihydrophthalate) is produced.

12. A process of claim 2 wherein the dienophile is bromomaleic anhydride so that 4,4'-thiobis(3,6-dihydrophthalic anhydride) is produced.

* * * * *